United States Patent
Happappel

(10) Patent No.: US 9,719,893 B2
(45) Date of Patent: *Aug. 1, 2017

(54) DNA EXTRACTION FROM SEEDS USING OSMOTICUM

(71) Applicant: Syngenta Participations AG, Basel (CH)

(72) Inventor: Ulrich Happappel, Slater, IA (US)

(73) Assignee: Syngenta Participations AG, Basel (CH)

( * ) Notice: Subject to any disclaimer, the term of this patent is extended or adjusted under 35 U.S.C. 154(b) by 258 days.

This patent is subject to a terminal disclaimer.

(21) Appl. No.: 14/359,238

(22) PCT Filed: Nov. 28, 2012

(86) PCT No.: PCT/US2012/066751
§ 371 (c)(1),
(2) Date: May 19, 2014

(87) PCT Pub. No.: WO2013/082081
PCT Pub. Date: Jun. 6, 2013

(65) Prior Publication Data
US 2014/0336372 A1    Nov. 13, 2014

Related U.S. Application Data

(60) Provisional application No. 61/564,138, filed on Nov. 28, 2011, provisional application No. 61/677,514, filed on Jul. 31, 2012.

(51) Int. Cl.
| | | |
|---|---|---|
| C07H 23/00 | (2006.01) | |
| B02B 5/00 | (2006.01) | |
| B02B 1/00 | (2006.01) | |
| B02B 3/12 | (2006.01) | |
| B02C 7/18 | (2006.01) | |
| B02C 9/00 | (2006.01) | |
| B02C 11/00 | (2006.01) | |
| A01H 5/02 | (2006.01) | |
| G01N 1/28 | (2006.01) | |
| B02C 23/18 | (2006.01) | |
| B02C 1/14 | (2006.01) | |

(52) U.S. Cl.
CPC ............. G01N 1/286 (2013.01); B02C 1/14 (2013.01); B02C 9/00 (2013.01); B02C 23/18 (2013.01); *G01N 2001/2866* (2013.01)

(58) Field of Classification Search
CPC ............ G01N 1/286; G01N 2001/2866; B02C 23/18; B02C 9/00; B02C 1/14
See application file for complete search history.

(56) References Cited

U.S. PATENT DOCUMENTS

| 2,530,272 A | 11/1950 | Thrasher et al. |
| 7,229,034 B2 | 6/2007 | Feazel et al. |
| 2007/0207485 A1 | 9/2007 | Deppermann et al. |
| 2009/0286301 A1 | 11/2009 | Tao et al. |
| 2011/0062256 A1 | 3/2011 | Cope et al. |
| 2016/0115472 A1* | 4/2016 | Hannappel .............. A01H 1/04 506/7 |

FOREIGN PATENT DOCUMENTS

| WO | 2003062462 | 7/2003 |
| WO | 2010108082 | 9/2010 |

OTHER PUBLICATIONS (R) Dellaporta et al., "A Plant DNA Minipreparation: Version II," Plant Molecular Biology Reporter, 1(4), 19-21, (1983).*
(S) Paris et al., "Cereal DNA: A Rapid High-throughput Extraction Method for Marker Assisted Selection," Plant Molecular Biology Reporter, 18(4), 357-360 (2000); only CAPLUS abstract supplied.*
Shao et al., The Outemost Cuticle of Soybean Seeds: Chemical Composition and Functino during Imbibition. Journal of Experimental Botany, Jan. 11, 2007, 58(5):1071-1082.
Gao et al., Development of a Seed DNA-based genotyping system for marker-assisted selection in maize. Mol. Breeding, May 22, 2008, 22:477-494.
International Search Report dated Jun. 17, 2013 for International Patent Application No. PCT/US2012/066751.
Von Post Rebecka et al., "A high-throughput DNA extraction method for barley seed," Euphytica 130: 255-260 (2003) Kluwer Academic Publishers, Netherlands, Jan. 1, 2003 XP002448173.
Sagi, Naoki et al., "Comparative Evaluation of Three Different Extraction Methods for Rice (*Oryza sativa* L.) Genomic DNA", Journal of Agricultural and Food Chemistry (2009) 57, 2745-2753 XP055210459.
Supplementary Partial European Search Report EP12854523, Sep. 10, 2015.

* cited by examiner

*Primary Examiner* — Lawrence E Crane
(74) *Attorney, Agent, or Firm* — Christopher Leming

(57) ABSTRACT

The invention relates to methods of extracting DNA from seeds, said method comprising pretreating said seeds by soaking the seeds in a pretreatment solution comprising an alkali in a concentration sufficient to soften said seed; crushing said seeds; extracting said DNA from said crushed seeds. Methods also relate to the use of pretreatment solutions which further comprise an osmoticum. A method of fragmenting plant material such as seed, a method of recovering extraction medium from seed fragmentation and a process of extracting a seed component from crushed seed material are also described.

8 Claims, 8 Drawing Sheets

DNA EXTRACTION FROM SEEDS USING OSMOTICUM

RELATED APPLICATION INFORMATION

This application is a 371 of International Application No. PCT/US2012/066751, filed 28 Nov. 2012, which claims priority to U.S. Provisional Patent Application No. 61/564,138, filed 28 Nov. 2011, and U.S. Provisional Patent Application No. 61/677,514 filed 31 Jul. 2012 the contents of which are incorporated herein by reference herein.

BACKGROUND

Understanding a seed's content or genotype is useful in a variety of agricultural practices from plant genetic engineering to conventional plant breeding. The seed content reveals information that can be employed to produce, select or develop new plants with improved agronomic, horticultural or economic characteristics or traits. Testing seeds or parts of seeds for selected characteristics often requires extraction and analysis of DNA.

Seeds tend to have a natural protection against destructive forces. Maize, cereals, soybeans, rice, soybeans and other beans, melon, pomegranate, sunflower, safflower, iodized poppy, sesame, cardamom, celery, dill, fennel, nutmeg, and plantain along with other vegetable, crop and flower seeds often are very hard. Because of this protection, crushing hard seeds frequently requires significant mechanical force. Applying manual force to crush seed is slow, difficult, and hard on the lab equipment.

Testing seed lots for purity and other seed contents often requires the extraction of DNA from a very large number of single seeds. Therefore there is the need for an efficient system for high-throughput DNA extraction. To extract DNA from seeds, they must first be fragmented. Several fragmentation methods exist seeds can be manually crushed with a mortar and pestle.

Alkaline lysis is a plasmid extraction technique which was invented by Birnboim and Doly: Cells (*E. coli*) are disrupted in an alkali solution. The high pH not only lyses the cells but also denatures genomic and plasmid DNA. In the next step the solution containing the lysed cells is neutralized, where the small plasmid DNA, which is circular and supercoiled, snaps back to being double-stranded. A large amount of the genomic DNA, however, stays linear and attaches to the cellular debris. During the following centrifugation step most of the genomic DNA is therefore lost in the pellet.

Sodium chloride has been found to decrease water uptake of seeds (Nizam, I. (Sep. 7, 2011), "Effects of salinity stress on water uptake, germination, and early seedling growth of perennial ryegrass," African Journal of Biotechnology 10(51):10418-10424).

All publications and patent applications referred to herein are incorporated herein by reference to the extent not inconsistent herewith for purposes of written description and enablement.

SUMMARY

The present invention describes a device and methods of seed fragmentation including using elements such as crushing pins and/or steel beads. The invention includes their use in making the internal components of the seed more available and accessible.

This invention also includes methods for preconditioning the seed prior to fragmentation which increase the ease of seed fragmentation and increases the DNA yield. One embodiment of the invention employs a seed crusher, which eliminates the need for separator devices by employing a seed preconditioning step. This invention provides a seed crusher adapted for crushing seeds in individual wells or seed holding containers and/or plates, which then can be employed for testing. The seed crusher according to the present invention has a well plate with at least one well for receiving a male crushing element; a well plate, where each well has an open top and a closed bottom and a specific length from said top to said bottom; (c) a horizontal die plate comprising at least one male crushing element positioned thereon to fit within at least one well of said well plate; (d); said male crushing element sized to be positioned within a well; (e) a press for bringing together the die plate in a position relative to the well plate such that the male crushing element enters the well such that in the mated position the male crushing element does not engage said well bottom.

Either or both of the plates, the well plate and/or the die plate can be moveable, alternatively one plate can be moveable and the other can remain fixed. In another embodiment the well plate has a plurality of wells, which can be arranged in an array, and the die plate comprises a plurality of male crushing elements which can be fixed in a similar array. The seed crusher device comprises a die plate has a plurality of male crushing pins, i.e. a pin aligned for mated entry into each well. Each well plate has a plurality of wells that serve to hold and support the pretreated seed. Use of pretreated seed is to prevent well breakage. Pretreated seed require less pin force during crushing; thus decreasing the chance that a crushed seed is pushed through the bottom of a well.

In one embodiment, the male crushing elements are rinsed, to remove remnant seed material, between each mateable engagement with a seed in a well. In another embodiment the male crushing element has a cascade of fluid liquid or airflow removing remnant as the pin moves from the mated position to the unmated position. In other words, as the seed crushing element is withdrawn or is withdrawing from the well, the liquid or air is applied to the pin such that the crushed seed material on the crushing element is deposited into the well with the now crushed seed. In another embodiment more a one die plate is used and the die plate that is not being used is cleaned of remnant seed prior to another use. The die plates can rotate through a wash cycle adapted to remove remnant when not in the seed crushing position. In yet another embodiment the male crushing element is disposable and is discarded and a replacement male crushing element and or die plate is employed.

The invention also provides a method of crushing seed by placing one or more pretreated seeds in each well and operating the seed crusher apparatus to mate the crushing element with the pretreated seed. The invention further proves a method of pretreating seed, crushing seed, extracting one or more constituents from crushed seed and analyzing or testing the seed constituents within the well.

The present invention also describes a device and methods of seed fragmentation including using mechanical crushing of preconditioned seeds. In one embodiment of the invention the seeds are softened by soaking in water, or SDS or an extraction buffer, such as the modified Dellaporta, this soaking can occur at elevated temperatures like 65° C. The objective of the pretreatment is to soften the seed so that the force of the mechanical crushing does not break the vessel in which the seed is housed. Additionally, after the pin crush is employed if further seed fragmentation is desired then reducing elements such as steel beads are employed for fragmenting of the preconditioned seed.

In another embodiment of the invention, the seeds are biochemically preconditioned to a sufficiently softened state that the pin crusher is not employed and reducing elements such as steel beads are employed as the force for fragmenting the preconditioned seed. An advantage to this embodiment is that in a given time more seeds can be processed with reducing elements than can be processed, in that same time, using the pin crusher.

Generally, the invention broadly relates to methods of fragmenting seed which employ mechanical devices such as crushing pins or other crushing devices with a preconditioned hard seed. Methods of preconditioning the hard seeds, to soften the seed for more effective fragmentation, which are adapted to enhance extracted DNA yields and/or DNA quality are shown. One method of preconditioning seed is to employ a seed-softening alkali soaking solution used for pretreatment of the seeds prior to employing reducing elements to further fragment the seed to enhance extracted DNA yield from the alkali-soaked seeds.

However, these seeds' uptake of large volumes of alkali can cause some loss of DNA yield. It is well known that osmotica regulate the water uptake by seeds. When an osmoticum is added to the alkali soaking solution it can visually be seen that seeds are less swollen but the seeds are softened enough so that they can be completely fragmentized with steel beads. Thus extracted DNA yield from alkali-soaked seeds can be significantly increased by adding an osmoticum to a seed-softening alkali soaking solution used for pretreatment of the seeds prior to fragmentation of the seed. Not intending to be bound to any theory, it seems that less DNA is denatured and resulting in higher DNA yield.

The osmoticum inhibits and reduces liquid uptake by the seeds, while still rendering the seeds weakened enough to be crushed with steel beads, without requiring the use of crushing pins or other crushing devices. The osmoticum can be sodium chloride or other osmotica known to the art. Soaking for a period of time between about 12 and about 25 hours in pretreatment solutions comprising about 0.1 M to about 0.1 M sodium hydroxide and about 1 to about 5 M sodium chloride at temperatures between about 22° C. and 65° C., softens the seed to allow satisfactory crushing with the steel beads, while increasing the yield of extracted DNA. Thus if larger yields of DNA are required, an osmoticum can be added to reduce the seeds uptake of the soaking solution.

An alternative method to achieve the increased DNA yield from the alkali softening solution is to employ decreased volumes of alkali. When the volume of liquid available is below the seed's potential capacity to easily uptake liquid, less DNA seems to be denatured leading to better DNA yield.

Generally, the invention broadly relates to methods of fragmenting seed which employ mechanical devices such as crushing pins or other crushing devices with a preconditioned hard seed. Methods of preconditioning the seeds, to soften the seed for more effective fragmentation, which are adapted to enhance extracted DNA yields and/or DNA quality are also shown.

Turning to the mechanical device such as crushing pins this invention provides an improved seed crusher adapted for crushing seeds in individual wells or seed holding containers and/or plates. The crushed seeds within the containers can then be directly employed for DNA extraction or further fragmented prior to DNA extraction.

Thus one embodiment of the present invention is a process of crushing seed to form crushed seed material comprising the steps of: pretreating seed material in a well; crushing the pretreated seed material in an automated system comprising a horizontal die plate with at least one vertical pin adapted to enter into each well and crush the seed therein, extracting a seed component for analysis from said well.

Yet another embodiment is a seed crusher device for seed fragmentation, comprising: a well plate with a well with a well bottom, said well adapted for receiving plant tissue material such as seed; a die plate adapted to admit at least one pin, to enter into the well; and a press for bringing together the die plate with a crush pin to enter the well and crush said received seed between the pin and the well bottom. The crush pin is part of a die plate wherein the well plate is moveable and the die plate is in a fixed position or alternatively the well plate is in a fixed position and the die plate is moveable.

To facilitate further fragmentation of the seed material the well plate has one or more reducing elements deposited within at least one well. Optionally a device for shaking, rotating or vibrating the reducing elements within the well can be employed for fragmentation of the seed material. This can be a part of the crusher device or a stand-alone device. In one embodiment this platform is part of the crusher device and it that shakes, rotates, or vibrates the reducing element within the well.

This invention encompasses a method of recovering extraction medium from fragmented seed, said method comprising the steps of: shaking at least one seed in a well with reducing element for seed fragmentation; delivering extraction medium in each well wherein said medium can dissolve fragmented seed components; and recovering the extraction medium. Optionally, after the extraction medium is added to the well the well plate is reshaken after delivering the extraction medium in the well and before recovering the extraction medium. The method of recovering extraction medium from the fragmented seed can include the preconditioning step of pretreating the seed by soaking the seed in an alkali solution, wherein the seed's hardness is decreased.

Thus a process of crushing seed material comprises the steps of: pretreating seed material in a well; disrupting the pretreated seed with the reducer elements with collision forces, and extracting a seed component for analysis from said seed material. This solution comprises sodium hydroxide, potassium hydroxide, or baking soda.

In yet another embodiment the seed crusher according to the present invention has a well plate with at least one well for receiving a male crushing element; a well plate, where each well has an open top and a closed bottom and a specific length from said top to said bottom; (c) a horizontal die plate comprising at least one male crushing element positioned thereon to fit within at least one well of said well plate; (d); said male crushing element sized to be positioned within a well; (e) a press for bringing together the die plate in a position relative to the well plate such that the male crushing element enters the well such that in the mated position the male crushing element does not engage said well bottom.

In another embodiment the well plate has a plurality of wells, which can be arranged in an array, and the die plate comprises a plurality of male crushing elements which can be in a similar array. The seed crusher device comprises a die plate comprising a plurality of male crushing pins, i.e. a pin aligned for mated entry into each well. Each well plate has a plurality of wells that serve to hold and support the pretreated seed. Use of pretreated seed is to soften the seed to prevent well breakage during crushing. Pretreated seed require less pin force during crushing; thus decreasing the chance that a crushed seed is pushed through the bottom of a well.

In yet a further one embodiment, the male crushing elements are rinsed, to remove remnant seed material, between each mateable engagement with a seed in a well. In another embodiment the male crushing element has a cascade of fluid liquid or airflow removing seed remnant as the pin moves from the mated position to the unmated position. In other words, as the seed crushing element is withdrawn or is withdrawing from the well, the liquid or air is applied to the pin such that the crushed seed material on the crushing element is deposited into the well with the now crushed seed.

In another embodiment more a one die plate is used and the die plate that is not being used is cleaned of remnant seed prior to another use. The die plates can rotate through a wash cycle adapted to remove remnant when not in the seed crushing position. In yet another embodiment the male crushing element is disposable and is discarded and a replacement male crushing element and or die plate is employed.

The invention also provides a method of crushing seed by placing one or more pretreated seeds in each well and operating the seed crusher apparatus to mate the crushing element with the pretreated seed. The invention further proves a method of pretreating seed, crushing seed, extracting one or more constituents from crushed seed and analyzing or testing the seed constituents within the well.

Another problem in analysis of DNA extracted from seeds such as maize seeds is seeds can only be fragmented with steel beads if they are softened. An additional problem with the DNA analysis is using an alkali pretreatment softening process prior to crushing results in DNA yields which have been relatively low, not always meeting the minimum quantity or quality standards required for some downstream applications, e.g., purity testing of seed lots. A high DNA yield is important when using simple DNA isolation protocols. If contaminants which inhibit downstream application are present after DNA extraction, the DNA-containing solutions have to be diluted enough so the contaminants will not interfere with the downstream applications (e.g., PCR). In order for this dilution step to be effective, there has to be sufficient DNA in the solution that the downstream applications can go forward.

It has been found that the extracted DNA yield from alkali-soaked seeds can be significantly increased by adding an osmoticum to the seed-softening alkali soaking solution. The osmoticum inhibits and reduces water uptake by the seeds, but the seeds are weakened enough to be mechanically crushed with steel beads only, without requiring the use of pins. The osmoticum can be sodium chloride or other osmotica known to the art.

Without wishing to be bound by any theory of the mechanism by which the present method operates, Applicant proposes that a possible explanation for the findings reported herein might be that the reduced water uptake by the seeds reduces the amount of DNA that is being denatured. Single stranded DNA binds to cellular debris and is lost during following centrifugation steps during DNA extraction.

Therefore, provided herein is a method for extracting DNA from seeds, the method of pretreating seeds by soaking them in a pretreatment solution comprising an alkali in a concentration sufficient to soften said seeds; and an osmoticum at a concentration sufficient to enhance the yield of the DNA compared to a process comprising pretreating the seeds only with an alkali; crushing the seeds; and extracting the DNA from the crushed seeds. In yet another embodiment of the present invention the efficiency of the crushing step can be improved by soaking seeds in temperatures elevated beyond room temperatures. These temperatures can range from room temperature 22° C. to 50° C. and up to 65° C. or higher.

Therefore, provided herein is a method for extracting DNA from seeds, the method of pretreating seeds by soaking seed in a limited quantity of pretreatment solution comprising an limited alkali solution in a concentration sufficient to soften the seed; sufficient to enhance the yield of the DNA compared to a process comprising pretreating the seeds with a larger quantity of alkali solution in a concentration sufficient to soften the seed; crushing the seeds; and extracting the DNA from the crushed seeds. This method can fragment the seed with a pin crusher, and/or using steel bead type crusher. This method can also fragment the seed with a bead type crusher. This method of fragmentation of the seed employs a step of shaking beads and seeds. Therefore, provided herein is a method for extracting DNA from seeds, said method comprising:

a. pretreating said seeds by soaking them in a pretreatment solution comprising:
  i. an alkali in a concentration sufficient to soften said seeds; and
  ii. an osmoticum at a concentration sufficient to enhance the yield of said DNA compared to a process comprising pretreating said seeds with an alkali;
b. crushing said seeds; and
c. extracting said DNA from said crushed seeds.

The process provided herein is useful for extracting DNA from seeds that are difficult to crush by mechanical means alone. For example, grains and fruits often have hard seeds that need to be softened before extraction is possible. Examples of such seeds with hard seeds of maize, grains such as barley, buckwheat, rice, wheat, bulgur, millet, rye, and rice, soybeans, and other beans, vegetables, other crop and flower seeds including melon, pomegranate, sunflower, safflower, iodized poppy, sesame, cardamom, celery, dill, fennel, nutmeg, and plantain. Many other seeds having hard seeds, from which DNA is desired to be extracted, are known to the art and can be used in the processes described herein.

The DNA extracted by the processes hereof can used for testing to determine components of the seeds, the genotype of the seeds, or for other purposes as known to the art. Such testing methods are known to the art.

Many methods of extracting, separating, isolating, and purifying DNA are known to the art.

The alkali component for the pretreatment solution can be any hydroxide donor known to the art that is capable of achieving a pH high enough to cause softening of the seed, e.g., a pH of about 12.0 to about 14.0, which will denature, but not damage, the DNA to be extracted. In embodiments the alkali is sodium hydroxide or potassium hydroxide. The alkali should be present at a concentration wherein DNA is extracted, and is strong enough to soften the seeds to facilitate crushing. In many embodiments, an alkali solution capable of softening the seeds is at a concentration of about 0.1 M to about 1 M; however, the concentration can also be higher or lower than these concentrations in certain instances.

An osmoticum is a substance that acts to supplement osmotic pressure in a plant or plant part or culture of plant cells. The osmoticum useful herein can be any substance or combination of substances known to the art to increase the osmotic pressure of a solution and prevent or inhibit uptake of liquid from the soaking solution the seeds without interfering with downstream extraction, isolation or purification of the DNA to be extracted. In embodiments, the osmoticum is selected from the group consisting of sodium chloride, potassium chloride, polyethylene glycol (PEG), mannitol, sorbitol and other sugar alcohols, and sucrose, provided that if downstream PCR is required, sucrose is not used in amounts that would inhibit the PCR. The osmoticum should be present in the pretreatment solution at concentrations sufficient to significantly reduce uptake of liquid from the pretreatment solution by the seed. Sufficient osmoticum is used for pretreatment of seeds from which DNA is extracted to increase the yield of extracted DNA over the yield achieved in previous DNA extraction processes in which lesser amounts of osmoticum (or no osmoticum) were used. In embodiments, the osmoticum is present in the pretreatment solution at a concentration between about 1 M and about 5 M.

The seeds are allowed to soak in the pretreatment solution for a period of time sufficient to allow osmoticum to work, and the alkali to soften the seed enough to facilitate crushing the DNA to be extracted. In some embodiments, this period of time is between about 12 hours and about 25 hours. The length of soaking can be shortened or lengthened beyond the 12 to 25 hours dependent on the hardiness of the seed. When the concentration of the alkali and osmoticum solution is adjusted upward or downward, the amount of soaking time required will be correspondingly less for stronger solutions or more for less concentration solutions.

The seeds are soaked in pretreatment solution at a temperature high enough to result in sufficient softening of the seed to facilitate crushing but not so high as to damage the DNA to be extracted. In embodiments, the soaking temperature is between about 22° C. and about 65° C.

Crushing of the seeds can be performed by the pins or with steel beads or any method known to the art. In some embodiments, the method comprises placing the seeds in a confined space and shaking them with size-reducing elements. A confined space is one having walls of sufficient surface area and wall strength to ensure that enough collisions between the size-reducing elements and the seeds occur to fracture the seed. In some embodiments, the confined space is a well of a well plate.

The size-reducing elements can be any particles of sufficient hardness to fragment the seeds by impacting them. Size-reducing elements useful herein can be selected from the group consisting of ball bearings, bee-bees, small pellets, stainless steel balls, carbide balls, objects with sphere-like shapes, made of ceramics, steel, copper, aluminum, or plastic, synthetic diamond, and other materials having sufficient hardness to break up the seeds. The particles can be spheroid or have other shapes including faceted shapes or shapes with points and/or edges to facilitate break-up of the seed.

In some embodiments, the crushing step is performed by a method comprising placing the seeds in wells of a well plate and exerting crushing pressure on them by contacting them with pins attached to a die plate configured to press the pins into the wells and crush the seeds.

The crushing step can also be performed in any confined space known to the art, such as a tube, pot, or other closed or open container having walls of sufficient strength to withstand the impact of the size-reduction elements and the seeds and seed fragments.

In at least one embodiment, the pretreatment solution is not separated from the seeds prior to crushing them. In another embodiment, the pretreatment solution is separated from the seeds prior to crushing them. In yet other embodiments, the pretreatment solution in contact with the seeds is replaced with a DNA extraction buffer or other liquid used for extraction of DNA prior to crushing the seeds.

In some embodiments, the pretreatment, crushing and extraction steps, or subsets of these steps, are automated, which can be modified by those of ordinary skill in the art without undue experimentation by adjusting the pH of the alkali pretreatment solution as described herein and adding an osmoticum to the solution, or, in processes not including pretreatment in a soaking solution, by adding a pretreatment step of soaking in an alkali and osmoticum solution as described herein.

DETAILED DESCRIPTION

Figure 1:
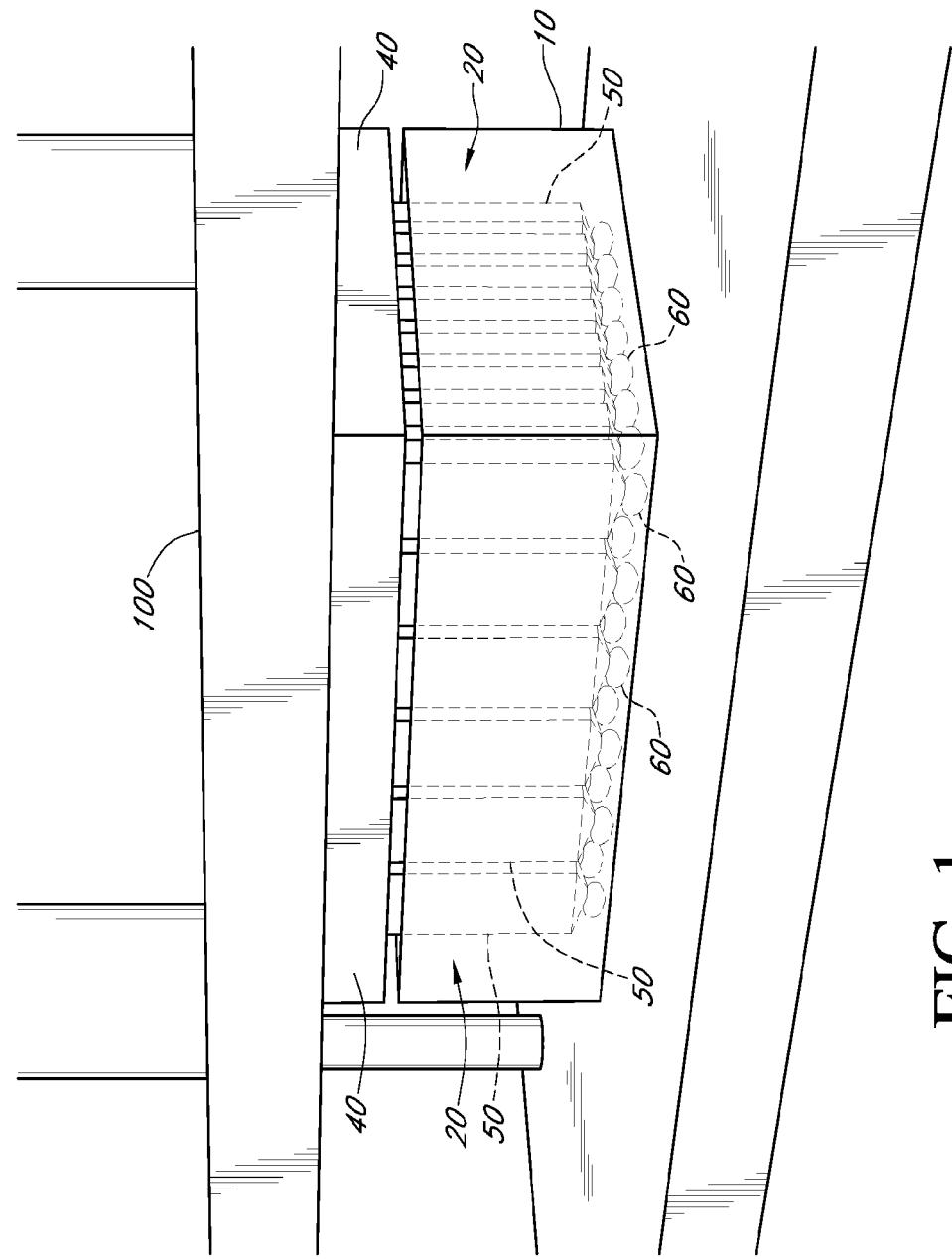
FIG. 1 is an illustration of components of a seed crusher. The die press, the die plate with a plurality of seed crushing pin elements is shown. The crushing pins are within the wells of a seed holding well plate in the crushing position. The pins are not engaging the well bottoms in this position.

Maize seed that is fully matured at harvest is a very hard seed, which is usually slightly flattened. To extract DNA the present invention provides seed fragmenting or crushing protocols and method of preserving DNA yields while decreasing the hardness of the seed such that the DNA from the fragmented seed can be readily extracted. One embodiment provides a device which mechanically crushes seed, using a seed crusher. This mechanical method of crushing includes pretreatment of the seeds. This pretreatment is in some embodiments is adapted to soften the hardness of the seed in in soaking solution of extraction buffer at pH 8.2, which maybe poured off of seed prior to crushing with pin crusher. The softening soaking solution is poured off to make space for crushing pins in the well. A smaller volume of a softening soaking solution avoids the pour off step, if most of the soaking solution would be taken up by seeds. The softening soaking solution is extraction buffer at pH 8.2; the alkali solution could be used but for most seeds the alkali solution would be so effective that the pin crusher would probably not be needed for fragmenting the seed.

Thus one embodiment of the present invention is a process of crushing seed to form crushed seed material comprising the steps of: pretreating seed material in a well; crushing the pretreated seed material in an automated system comprising a horizontal die plate with at least one vertical pin adapted to enter into each well and crush the seed therein, extracting a seed component for analysis from said well.

Yet another embodiment is a seed crusher device for seed fragmentation, comprising: a well plate with a well with a well bottom, said well adapted for receiving plant tissue material such as seed; a die plate adapted to admit at least one pin, to enter into the well; and a press for bringing together the die plate with a crush pin to enter the well and crush said received seed between the pin and the well bottom. The crush pin is part of a die plate wherein the well plate is moveable and the die plate is in a fixed position or alternatively the well plate is in a fixed position and the die plate is moveable.

To facilitate further fragmentation of the seed material the well plate has one or more reducing elements deposited within at least one well. Optionally a device for shaking, rotating or vibrating the reducing elements within the well can be employed for fragmentation of the seed material. This can be a part of the crusher device or a stand-alone device. In one embodiment this platform is part of the crusher device and it that shakes, rotates, or vibrates the reducing element within the well.

This invention encompasses a method of recovering extraction medium from fragmented seed, said method comprising the steps of: shaking at least one seed in a well with reducing element for seed fragmentation; delivering extraction medium in each well wherein said medium can dissolve fragmented seed components; and recovering the extraction medium. Optionally, after the extraction medium is added to the well the well plate is reshaken after delivering the extraction medium in the well and before recovering the extraction medium. The method of recovering extraction medium from the fragmented seed can include the preconditioning step of pretreating the seed by soaking the precon in an alkali solution, wherein the seed's hardness is decreased.

Thus a process of crushing/disrupting or fragmenting the seed material comprises the steps of: pretreating seed material in a well; disrupting the pretreated seed with the reducer elements with collision forces, and extracting a seed component for analysis from said seed material.

Preferably when the pin crusher is not used then the pretreatment softening solution used in the above process comprises sodium hydroxide, potassium hydroxide, or baking soda.

After crushing the preconditioned seeds in a well plate equipped with crushing pins, if necessary, the crushed seed can be subjected to shaking the preconditioned seeds with reducing elements such as steel beads, small ball bearings, or other hard small particles. In yet another embodiment the crushing pins are not necessary. In this embodiment the seed is soaked in an alkali solution, such as a sodium hydroxide solution. This softened seed material after being presoaked in an alkali solution i.e., the preconditioned seeds, is sufficiently soften to be adequately fragmented with just the use of reducing elements such as steel beads, small ball bearings, or other hard small particles.

With reference to FIG. 1 there is shown a plate 10 having a well 20 with a first open end 27. After a seed 60 is placed in a well 20, a pin 50 attached to a die plate 40 enters into the well 20. FIG. 1 shows the die plate 40 being in a die press 100, which provides sufficient force on the die plate 40 to crush the seed 60 in the well 20. After the seed 60 is crushed with the pin 50, the seed appears as crushed particles of seed. Next the pin 50 withdraws from the well 20. The plate 10 is removed and pin 50 is rinsed of seed matter. Alternatively the pin 50 can be rinsed, with rinsate flowing into the well, and then pin 50 is removed for the area around the specific well 20 that specific pin had engaged.

Figure 2:
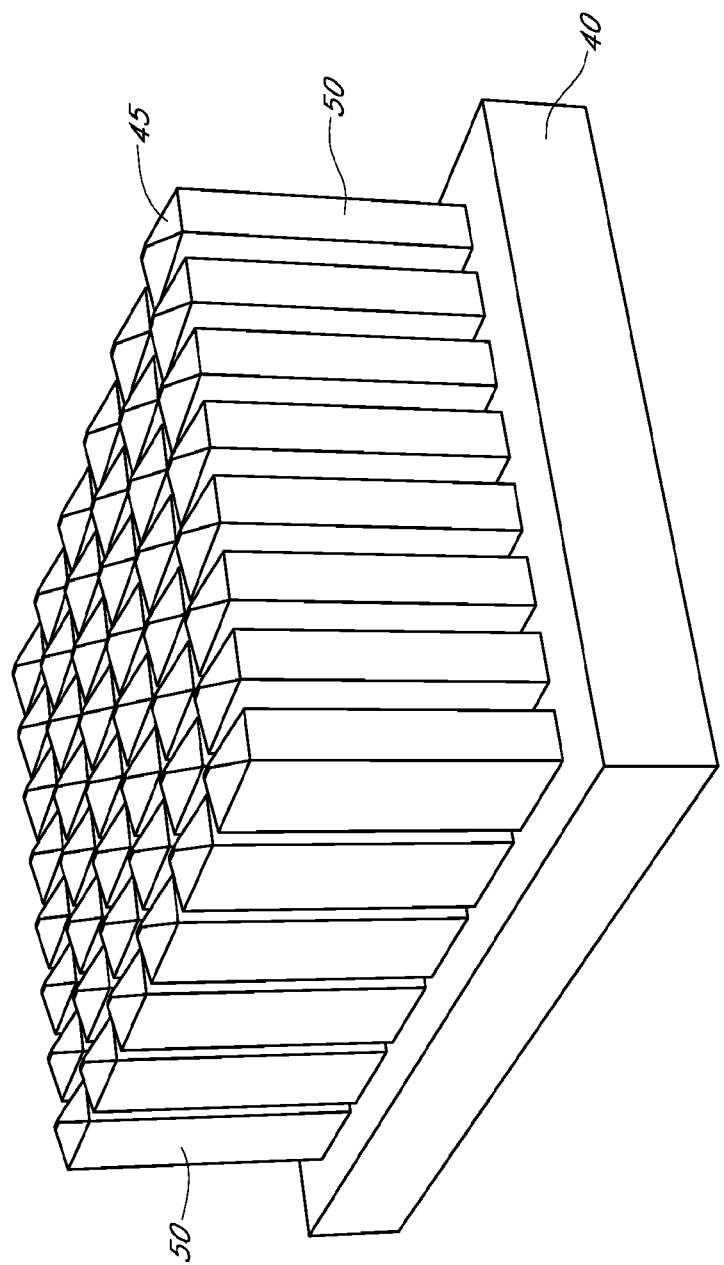
FIG. 2 is a side view illustration of a die plate with the plurality of seed crushing elements.
Figure 3B:
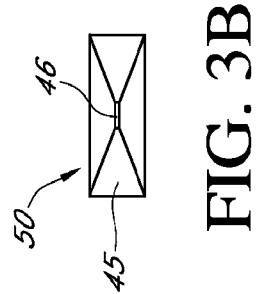
FIG. 3B is a top tip of a pin which is a seed crushing element.

With reference to FIG. 2 there is shown a side view of the die plate 40 with the pins 50. The FIG. 3A view shows the head portion 45 of the pins that are adapted to engage the seed. Another design for the head portion 45 of these pins is shown in FIG. 3B. In FIG. 3B, the tip 46 of the pin head is flattened. This results in a more even distribution of the crushing force across the engaged seed surface.

Figure 3A:
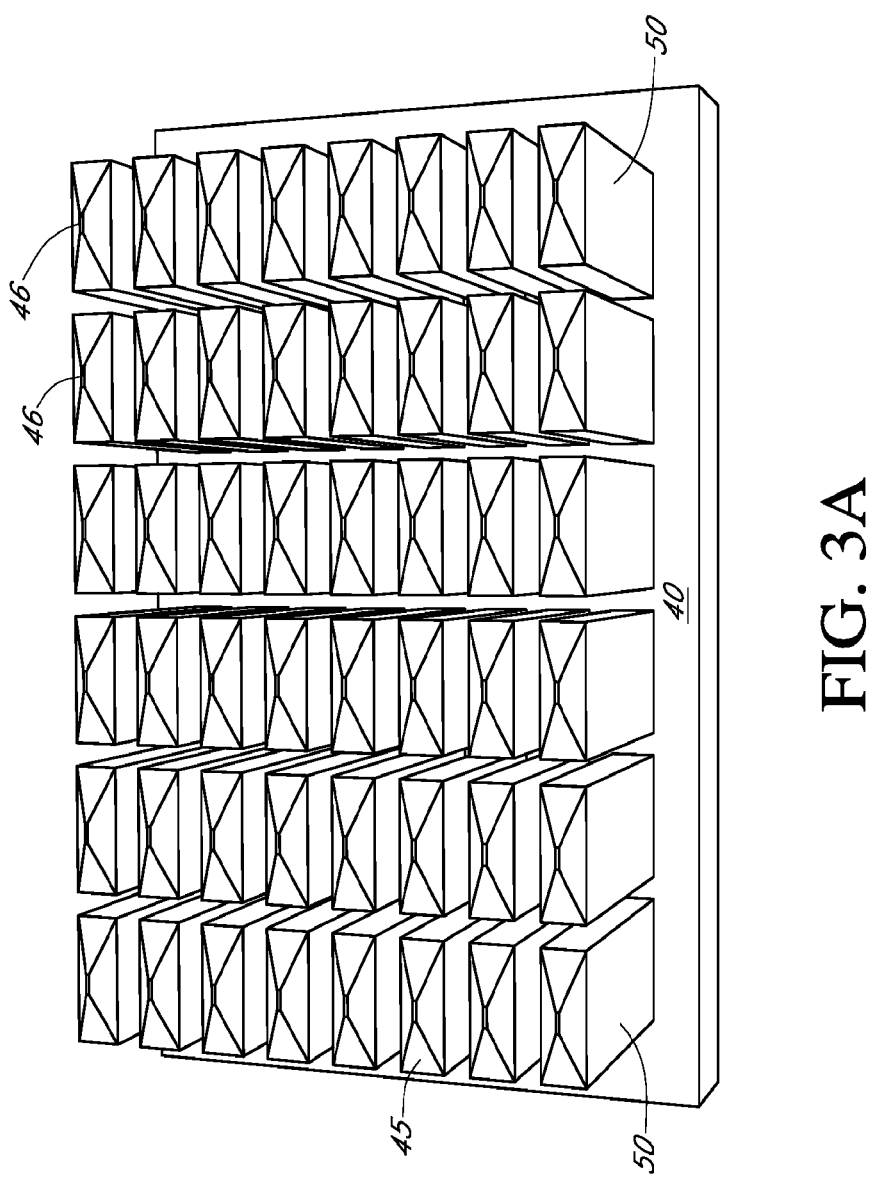
FIG. 3A is a top view illustration of a die plate with the plurality of seed crushing elements.

FIG. 3A shows a similar die plate as shown in FIG. 2, but from a top view. From this top view it can be seen that the pins 50 are aligned to engage the wells 20 of the well plate 10 shown in FIG. 1 and also in FIG. 4. The tips 46 of pins 50 are configured to approximate the shape of the bottom 25 of the wells 20. The four sided pyramid shape of the well bottoms 25 allow the tip 46 to move through the seed, crushing it with the downward force without having the tip 46 split open the bottom 25 of the well 20.

Figure 4:
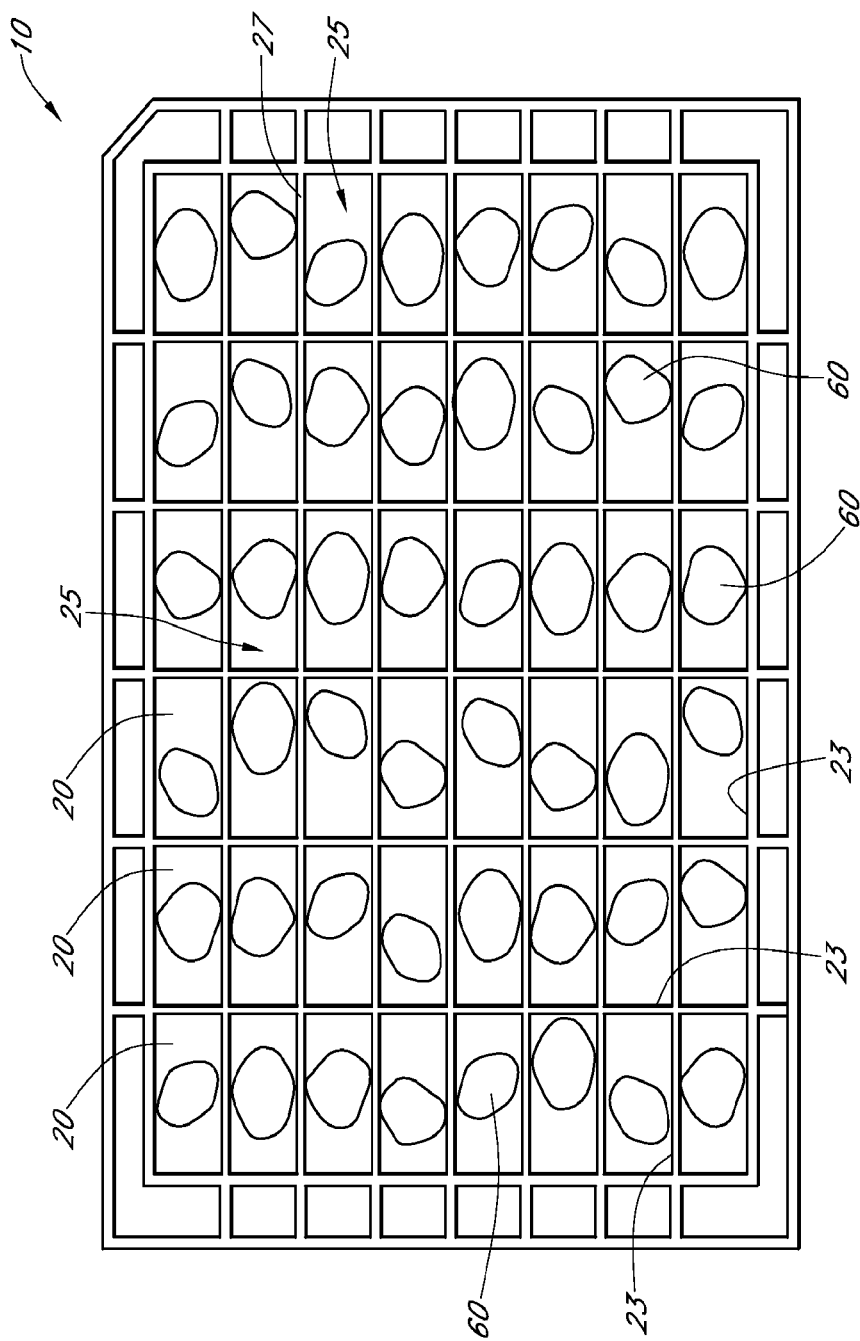
FIG. 4 is a top view illustration of a well plate with an open top and a four sided pyramid shaped bottom. This well plate has pretreated maize seed within the wells on the well plate.
Figure 5:
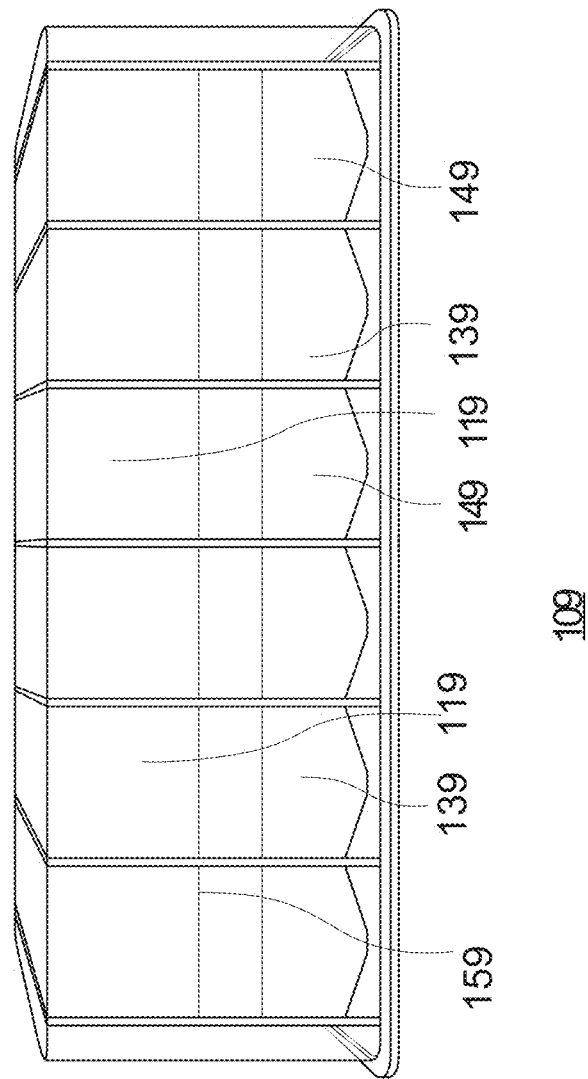
FIG. 5 depicts a well plate 109 containing crushed seeds in extraction buffer after centrifugation. Reducing elements 139 in the form of small steel balls are visible in each well 119, along with seed residue 149 at the bottom of each well. Supernatant 159 comprising DNA in extraction buffer can be seen above the residue in each well.

With reference to FIGS. 1, 4 and 5, the shape of the well plate 10, 109, as a rectangular preferably stackable plate with uniform wells 20, 119 (respectively). Each well 20, 119 has a rectangular well with a bottom 25 designed as an inverted four-sided pyramid. The well shape could be square, round, oval or other shape. Different shaped wells could use the same pins if the pins could enter and exit the wells without damage to the wells sides 23 or bottom 25. Alternatively, the shape of the pins 50 could be varied to more closely make the shape of the wells sides 23 and bottom 25. The specific shape of the wells is only important to the extent that the pin can crush the pretreated seed without damage to the well 20.

With reference to FIG. 4, the maize seeds shown in this figure are pretreated seeds. Maize seed that is fully matured at harvest is a very hard seed, which is usually slightly flattened seed. However, the seeds of FIG. 4 are pretreated seeds, which appear plump and slightly engorged. The process of crushing pretreated seed requires less force to get the through the tough exterior of the seed. After the seed is pretreated and soften the seed is subjected to the force of the die plate's pins, and the crushed seed has different components, which can be extracted and are used for testing purposes.

In an optional process, the pretreated seed is not crushed with the die plate. The seed is softened in a pretreatment of an alkali solution such as potassium hydroxide, or sodium hydroxide or the like for sufficient time to soften the seed material to the extent that the shaking of the plate 10 with size reducing element(s) within the wells reduce the seed to small particles. The size reducing element such as small ball bearings or other hard small particle or particles are placed within each well, the well is covered and vigorously shaking the pretreated seed and the particles within the well. The ball bearings act to break up the softened, pretreated seed, exposing the interior contents of the seed. The shaking or stirring of the capped well plate can be performed on a modified paint shaker type device, or on a rotatable surface adapted to hold the plate and stir or shake or swirl the contents of the wells.

The pretreated seed can be crushed in the well with the die plate and after that process the well plate can be removed from the die press and a size reducing element is placed in well 20 and shaken or stirred to further increase the surface area of accessible seed material by decreasing the particulate crushed seed size within the well 20 supported on the plate 10 which in this instance is horizontal.

The size reducing element may be a number of objects or a single object. In the one embodiment the element is formed of small spheres, such as ball bearings formed of metal, bee bees, small pellets, stainless steel balls, carbide balls, ceramic sphere-like shapes, steel, copper, aluminum, or plastic, synthetic diamond and the like. The element may also have facetted features the shape, and the like. The reducing element is adapted to fragment the seed material within the well 20 while the plate 10 is being vigorously shaken or stirred. By crushing seeds with beads or other size reducing elements the seed forms very minute particles from which significantly more DNA can be extracted when compared to larger crushed particles with less surface area. Also the reducing elements when shaken with the pretreated seed produce approximately the same amount of DNA per each seed. In contrast, larger seed particles with the added DNA extraction buffer, when shaken without the reducing elements can result in various amounts of extracted DNA quantity. This varied DNA amount may in turn, negatively affect the downstream DNA testing applications (e.g. SNP analysis).

The improved method of fragmentation of preconditioned seed allows the entire process of extracting material from a seed to be an automated process, from picking an ear with seed, or a head with sunflowers, through to shelling of the sunflower head or the shelling of the corn on the ear through shelling of the seed, wherein shelled seed is automatically placed in wells. Solution is fed into a pipetting system that imparts the soaking solution into the wells with the seeds material. The soaking of the seed material in the well can be at or above room temperatures. The seeds can be crushed with the die plate with its pins. Alternatively, the pin crushing step can be skipped.

Solution is fed into a pipetting system that imparts the soaking solution into the wells with the seeds material. The soaking of the seed material in the well can be at or above room temperatures. The seeds can be crushed with the die plate with its pins. Alternatively, the pin crushing step can be skipped. Regardless of whether the die plate was or was not used for the initial crushing of preconditioned seed, the seed can be fragmented with reducing element(s). The reducing elements, which are adapted to pound, crush, or grind to a powder, or to dust or just into small particles or a soft mass, can be added to each well 20. Aliquots of solution in combination with the reducing element(s) can be automatically loaded into the wells 20 in the plate 10. Then the transport system (not shown) can load the plates 10 onto a mechanical shaking device to engage the reducing elements with the soaked and softened seed in a shaking or stirring motion. Then the transport system can move the plate with the pulverized liquidated seed material within each plate through an automated DNA extraction and analyzing system. This allows the entire process from seed ear to DNA testing and analysis to be completed in an automated fashion.

Alternatively, this process of adding solution and/or reducing elements to the wells for seed soaking, transport of the plates for shaking, extraction and/or testing of the seed components within the wells can be performed manually in part or in total.

Plate

The horizontal plate is functional as a base for supporting a plurality of wells such that the plates are readily stored and stacked. The plate can be manually moved or it can be part of a transport system. Moveable plates may be transported through a system that loads seeds and identifies plates or wells or seed and records the necessary information in a retrievable form. The recordation of the location or order or arrangement is made in such a manner to allowing retrieval of needed information such as identity of the seed and its location within the well. The plate of wells can be made of any material, which can withstand the pressure needed to crush seed within the wells. The seed may be impacted with 2,000 to 7,000 pounds per square inch of pressure. Plastic is typically what the plate is formed from, however, metal or other materials which will not break or stress fracture under the crushing force can be employed in the plate.

Well

The function of the well is to provide a vessel for retaining the seed. The well as shown in FIG. 4 has a closed well end 25 and an open well end 27. The open well end is sized to receive the seed or part of the seed that is to be crushed. The other end is designed in configuration that is very similar to the shape of the crushing tip 46 shown in FIG. 3B of the pin 50. When the seed is loaded into the open well end 27 it comes to approximate the closed well end 25. The number of wells per plate can vary depending on the size of the seed loaded into the well plate. Typically the wells in the Figures are 48 well plates oriented in 8 columns and 6 rows. The closed well end 25 can take many different forms. The pin tip 46 is preferably adapted to the contours of the well end 25. The use of tetragonal inverted pyramid with a flatted bottom instead of a point as the well end 25 allows for a pin tip 46 with a small flattened crushing tip that focuses the crushing force in the seed. The well is selected from a composition of materials, often high density plastics that are capable of withstanding the pressure applied to the seed without cracking or forming small stress fractures. The well is used at a later stage in the process to hold liquids, so retention of the integrity of the well after the seed is crushed is important.

Die Plate

The function of the die plate is to provide a compressing, or pulverizing force to the seed material. Pistons, screws, levers, hydraulics or the like can drive this force. The die plate, which has a pin for each of the wells, transfers this force to the seed material. The pins, on the die plate, align with the positions of the wells in the plate and pressure from the die plate transfers through the pins into the seed material in the well 20. The pins engage and crush the seeds loaded into the wells of the plate.

The soaking solution might have to be removed before crushing, particularly if there is not enough space for pins and soaking solution. Alternatively, the soaking solution supplied is only sufficient to soften seeds such that the soaking solution is entirely taken up by the seeds.

The die plate is positioned within the press to permit the pins to enter the wells to a crushing depth but not to a depth, which would break the bottom of the well. The pins are adapted to allow for engagement with seed material, which is often presoaked and thus softened. The pins extend into the wells of the plate a sufficient length to crush the seed, but without reaching the bottom of the wells. The engagement of the pin with the seed in the well plate can be monitored and the plate and or die positioning can be adapted to best crush plates of seeds of varying size. As noted previously, the hardness of the seed and thus its resistance to crushing is impacted by the pretreatment with the solution. This pretreatment will reduce the amount of force necessary to crush the seed material. Additionally, seeds are different shapes. Seeds are formed as flats, rounds and smalls, and small medium and large, due to this variety it is helpful to be able to automatically or alternatively manually adjust the position of the seed plate and or the die plate, and the force being applied to the seeds. The adjustment will allow the various seed sizes to be subjected to sufficient pressure to be crushed while maintaining the integrity of the wells.

The press is configured to align the pins on the die plate with wells on the horizontal plate. To help with the alignment the die plate and/or the horizontal plate can be moveable such that the effect is that the pin is may be aligned within the well.

The press moves the die plate between the disengaged and engaged position relative to the wells in the plate. The die plate in FIG. 1 is moved using hydraulics, although it could also be moved manually. The FIG. 1 shows the seed in the well and the die plate in the engaged position. The engaged position places the pin within the interior of the well. The disengaged position has the pin outside of the well. A pin prior to crushing the seed or seed part in the well is slightly above the well opening, and a pin in the engaged position crushing the seed or seed part is within the sides of the well.

The die plate can be manually placed in the engaged position proximate the seed loaded wells and then the press can be employed to provide crushing force. Alternatively, the die plate can be automated to engage with seed loaded well to employ the crushing force. If the crushed seed material is clinging to the pin, the pin will have to be treated to avoid contamination between horizontal plates of wells. The remnant seed material remaining on the pin from crushing seed from a first well cannot remain on the pin prior to crushing the next well of the next plate. This remnant seed would contaminate the seed material in the next well, with seed material the first well. One method of avoiding such contamination is to use a separating material that remains between the seed and the pin. Another method is to rinse the seed material from the pin between each well engagement. The rinse can flow back into the well, or the rinse can occur outside of the well area. The rinse stream can spray in rotation or be a spray from the pin side of the die plate or the rinse can be adapted to stream down the sides of each pin washing the rinsate and residue crushed seed material into the well holding that seed. The rinse can occur by removing the pin from the wells and then dipping the pins into a bath of water to remove seed contaminates. Alternatively, if the pins are sheathed, then the sheath which has the remnants attached there to can be rinsed or disposed of after each use. This process of avoiding interwell seed contamination can be manual or automated.

Due to the sensitivity of technology for seed analysis, cross contamination of seed material between wells will negatively affect the accuracy of the seed composition analysis, therefore techniques for avoiding cross contamination must be employed. In yet another embodiment, the pins can be disposed of after each use if they are made of a disposal material. Alternatively a flexible material that is not readily pierced, such as plastic and other polymer sheets can cover the well tops so that upon entrance of the pin into the well, this material sheaths the pin. Upon disengagement of the pin from the well the sheet or the used portion of a continuous roll of the plastic like or flexible material can be removed from the plate and disposed of, stored or rinsed if it is reusable. Then a new portion or a new sheet can be used for the next plate to cover or effectively coat on the pins prior to the next pin-well engagement.

The pins can be removably attached to the die plate. This allows for disposal and replacement, ease of cover removal, more complete rinsing or cleaning procedures. The pin can be made of plastics, metal, polymers, wood, stone, ceramic and other synthetic materials. It can also be made with a hollow bore within the pin that can be used for ease of transporting rinsing material, or to reduce the cost of a disposable pin. Alternatively, the pin can be formed of as a solid piece of material such as plastic or metal. Regardless, of whether it is solid or has a hollow interior the pin must be formed to with stand the pressure so it does not shatter or crack. Size and shape (orthogonal like bottom of the wells) of these pins shown in the figure have the effect that almost no crushed seed sticks to them. Thus avoiding most of the cross contamination of seed material between wells.

The seed-engaging end of the pin is formed to focus the pressure. Seeds come in a variety of shapes, soybean, canola seeds are spherical, maize, wheat, oats, triticale, barley, grass seeds are teardrop shaped though maize seed can be very spherical like popcorn seeds, peanut seeds are oblong, and sunflower, and many melon seed, like watermelon seed are fairly flat.

The pins engaging end is formed as a four faced, inverted pyramid with either a pointed bottom or a small-flattened center area at the bottom of the inverted pyramid. The flattened area is less likely to penetrate any pin covering material, if that is being used to avoid seed interwell contamination. The face of the engaging end of the pin can be selected according to the shape of the seed that is being crushed, to maximize the crushing impact while minimizing the pressure need to crush the seed material. It is also designed to reflect the shape of the bottom of the well being used.

The pressure needed to crush the material with the pin can clearly be altered by pretreatment of the seed material with alkali solution also.

This invention encompasses the method of using the crushed seed material to extract DNA, or other seed components, like protein, oil, carbohydrates, fungus, spores, etc. for testing. The components for the crush material are used to perform analysis of this extracted material.

After the seed is crushed by the seed crushing device, an extraction medium is often delivered to the wells with the crushed seed material and then the extracted material is recovered and tested. The extraction process is often a Dellaport method or a modified Dellaporta method for DNA extraction. The extraction method can be a useful method for extracting the desired material for analysis from the crushed seed. The analysis of the extracted material can detect seed pests, seed components, seed composition, or other properties associated with the extracted material. The extraction liquid added to the crushed seed material within the well is selected based what must be extracted to run the analysis that is being tested. The extraction medium can be delivered by a pipette or by a robotic system.

In other embodiments of the present invention, the pin crushing device can be employed or other fragmenting devices with less effort and more efficiently with the following seed pretreatments.

The seed is softened by pretreatment involving soaking the seed in an alkali solution such as potassium hydroxide, sodium hydroxide or other alkali known to the art for a sufficient period time to soften the hard seed material to the extent that the shaking of the well plate with size-reducing element(s) within a confined space such as the wells of a well plate reduces the seed to small particles. The pretreatment solution also contains an osmoticum, such as sodium chloride or other osmoticum known to the art, such as potassium chloride, polyethylene glycol (PEG), mannitol, sorbitol or other sugar alcohols, or sucrose (provided that if downstream PCR is to be performed, sucrose is not used in amounts sufficient to substantially interfere with the PCR) to increase the osmotic potential of the solution such that uptake of liquid from the pretreatment solution by the solid seed components is reduced sufficiently to increase DNA yield in subsequent extraction steps.

FIG. 5 shows a plate well 109 comprising multiple uniform wells 119 in which maize seeds were soaked in a pretreatment solution containing 3M sodium chloride as the osmoticum and 0.1 M sodium hydroxide as the alkali for 21 hours at 35° C. The pretreatment solution was then removed and replaced with a modified Dellaporta DNA extraction buffer, several steel beads 139 were added to each well, and the seeds were crushed in situ by agitation of well plate 109. After centrifuging well plate 109, seed residue 149 was separated from supernatant 159 which contained the extracted DNA.

The size-reducing elements 139, such as one or more small ball bearings or other hard small particles, are placed within each containing pretreated seeds to be crushed. The well is covered and vigorously shaken, e.g., in a paint shaker, with the pretreated seeds and the ball bearings within the well. The ball bearings act to break up the softened, pretreated seed, exposing the interior contents of the seed. Shaking or stirring of the capped well plate can be performed on a modified paint shaker type device, or on a rotatable surface adapted to hold the plate and stir or shake or swirl the contents of the wells.

In embodiments the size-reducing elements are small spheres, such as ball bearings formed of metal, bee-bees, small pellets, stainless steel balls, carbide balls, objects with sphere-like or other shapes, made of ceramics, steel, copper, aluminum, or plastic, synthetic diamond or other materials having sufficient hardness to break up the seeds. The particles can also be faceted or shaped with points or edges to facilitate break-up of the seed. The size-reducing elements are adapted to bombard the seed material within the wells 119 while the plate 109 is being vigorously shaken or stirred. When the seeds are crushed with beads or other size-reducing elements, the seeds form very minute particles from which significantly more DNA can be extracted compared to larger crushed particles. Also the size-reducing elements when shaken with the pretreated seeds produce approximately the same amount of DNA from each seed. In contrast, larger seed particles with added DNA extraction buffer, when shaken without size-reducing elements, can result in various amounts of extracted DNA per seed. This variation in amount of extracted DNA may in turn negatively affect downstream testing applications (e.g., SNP analysis).

The pretreatment process described herein in can be used to increase DNA yield following seed crushing processes as described above, in which crushing of the seeds was done in the wells of a well plate, the crushing was done both using pins and steel beads. The well plate with beads was placed on a shaking platform, such as a paint-shaking device. The well size determined the number of steel beads to be placed in each well as size-reducing elements. In an embodiment, six steel beads were added to each well. Four beads would also work. Using six beads it took only four minutes of shaking in a paint shaker to achieve a desirable particle size for the seed fragments. With fewer beads, the shaking step can be repeated if not all seeds are sufficiently fragmented or if the fragments are not uniformly of a desired size. After the plate had been shaken, and the presoaked, crushed seed material was further disrupted by the impact of the steel beads shaking within the wells, approximately 50 to 100 times more DNA was extracted, than when the pin-crushing process was used alone. Variation of DNA quantity obtained from single seeds was thus significantly reduced. Use of the pretreatment method described herein further increases the quantity of DNA obtained from each seed.

The entire process of extracting material from a seed can be an automated process, from picking an ear of maize with seed on the ear through shelling of the seed, wherein shelled seed is automatically placed in wells. The pretreatment solution containing the alkali and osmoticum can be fed into a pipetting system that imparts the soaking solution into the wells with the seed material. In embodiments, the soaking solution containing alkali and osmoticum is removed from the wells after a period of time required to soften the seed enough for crushing, and replaced with an extraction buffer. In embodiments the pretreatment solution is poured off the seed material and the crushing is performed in the absence of solution. Alternatively, in embodiments the crushing can be performed while the seeds remain in the alkali/osmoticum pretreatment solution, so long as sufficient DNA yield can be produced for the required downstream applications.

In embodiments, the seeds can be crushed with a die plate with pins; alternatively, the pin crushing step can be skipped. Regardless of whether or not a die plate is used, size-reducing element(s), which are adapted to pound, crush, or grind the seeds to a powder, dust, or into small particles, or a soft mass, can be added to each well 119. Aliquots of pretreatment solution in combination with the reducing element(s) can be automatically loaded into the wells 119 in plate 109. Then a transport system (not shown) can load the plates 109 onto a mechanical shaking device to engage the size-reducing elements 139 with the soaked and softened seed in a shaking or stirring motion. The transport system can move the plate with the pulverized liquidated seed material within each plate through an automated DNA extraction and analyzing system. This allows the entire process from seed to DNA testing and analysis to be completed in an automated fashion.

After the seed is crushed by the seed crushing device, an extraction medium is often delivered to the wells with the crushed seed material and then the DNA is recovered and tested. The extraction process is often a Dellaporta method or a modified Dellaporta method. The extraction method can be any useful method known to the art for extracting DNA for analysis from the crushed seed. The analysis of the extracted material can detect seed genotype, seed pests, seed components, seed composition, or other properties associated with the extracted DNA. The extraction medium can be delivered by a pipette or by a robotic system.

For increasing the efficiency of the extraction of the DNA from the crushed seed, the extraction medium can be agitated along with the size-reducing element(s) in a shaking or stirring or centrifuging type device. Decreasing the particle size of the seed material increases interfacial surface area, increasing the active bonds in the emulsion that is formed, which increases the viscosity of the medium as the particles interact more and tightly bond to each other. This increases the recovery of extracted DNA from the crushed seed material, which can be used for testing and further analysis.

Alternatively, the processes of adding pretreatment solution, extraction buffer, and/or reducing elements to the wells for seed soaking, transport of the plates for shaking, extraction and/or testing of the DNA within the wells can be performed manually in part or in total.

The processes described herein encompass methods of using the crushed seed material to extract DNA for testing or other use.

EXAMPLES

Example 1

1. Presoaked Seeds Crushed with Pin Disrupted with Reducing Element

Maize seeds which were soaked in solution, for this experiment sodium dodecyl sulfate (SDS) that washes off any seed treatment on the seed was employed. The extraction buffer also contains Tris, HCl and EDTA. SDS softens the seeds, more efficiently than water. Any soaking solution, including $H_2O$, which does not interfere with the downstream applications of the crushed seed material can be employed, if it softens the seed material. Soaking time depends on the hardiness of the kernels. In this experiment, the seed material was soaked for 24 hours at 65° C. The temperature can be higher or lower, even room temperature can be used, but in some experiments seeds were not efficiently softened at this temperature.

The 1500 ul sodium dodecyl sulfate buffer was used to pretreat the seeds. 1500 ul was an amount sufficient to cover the surface of the largest corn seeds. Additional liquid can be added if needed to cover the seed material within the wells. Some liquid was absorbed into the seed material, but not all of the liquid. Prior to crushing the seed, the soaking solution can be poured off of the seed material, as there may not be enough room for the soaking the solution and pin within the well. Overflow of this solution into other wells should not occur.

Alternative approaches not used in this experiment but also possible is to soak seeds in 400-600 ul of DNA extraction buffer. Most of the solution would be absorbed (depending on seed size), and seed could be crushed or alternatively just shaken. Assuming the seed would be crushed then slimmer pins than showing in the figures would possibly be employed. These somewhat slimmer pins relative to the well size could be found to be useful in this process.

The seed soaking material was selected to compliment, or are the least not interfere with the downstream testing of the seed material. In experiment one, the DNA composition of the seeds were being analyzed downstream, so DNA extraction buffer was an appropriate seed soak. However, to analyze different types of seed composition (i.e. not DNA) like oil or protein the soaking solution must be different. The soak must be adapted to the downstream testing and analysis.

As was shown in FIG. 1, there were pretreated soaked seeds, which were crushed with pins. The only purpose of the seed soaking pretreatment was to soften the seeds so that they can be easily crushed with the pins and then disrupted if necessary.

The pretreated seeds were subjected to the force on the pin applied with a hydraulic press. The pin was removed from the crushed seed. The seed remnant on the pin when extracted from the well was not rinsed into the well. The pins were rinsed in a location separate from the well plate. The well plate can be shaken with the extraction buffer or alternatively reducing elements such as steel beads can be added to each well of the plate, either process will work. The well size determined the number of steel beads. Because the well size was that shown in the figures, in this experiment six steel beads were added to each well. Four beads would also work but reduction of the ball number may decrease of the particulate size of the seed. Also by using six balls the time required to get desirable seed size crushed was only 4 minutes in a paint shaker. With few ball bearings used this shaking step might have to be repeated if not all seeds are sufficiently reduced in crushed size. Repetition of the shaking of the bead in the wells in the paint shaker is also an option if the seed particulate size is not sufficiently reduced using 6 beads or other pellet like material.

The well plate with beads was placed on a shaking platform, such as a paint-shaking device. After the plate had been shaken, and the presoaked crush seed material was further disrupted by the impact of the steel beads shaking within the wells approximately 50 to 100 times more DNA was extracted, then using the pin crushed process only. Variation of DNA quantity between single seeds is reduced significantly.

In this experiment, a modified Dellaporta extraction solution was used, the solution contained SDS, Tris and EDTA. The amount added depends whether the DNA was extracted manually or with robotics. In this experiment, the DNA was extracted by employing robotics. Robotics needs approximately (1500 ul). Experiments with manual extraction usually use about 800-1000 ul. The amount is adjustable. A supernatant was formed after centrifugation of the crushed seed material and the SDS extraction solution. This supernatant contained the DNA, which was transferred for addition testing steps.

In this experiment using the Dellaporta, after adding the extraction buffer and shaking the extract with steel beads in the well, $NH_4CH_3COO$ was added to the well. The well plate was briefly shaken again, and then centrifuged for 20 minutes. An aliquot of the supernatant (which contains the DNA) from each well was transferred to a new plate (e.g. a 96 well block (combining 2 48 well blocks (in which seeds have been crushed). In each of the wells was added an alcohol (isopropanol or ethanol) and alcohol precipitation of DNA was performed. This is a well-known standard procedure. Although this specific protocol was employed for extracting DNA from the crushed seed material, any DNA extraction protocol can be applied to generate the necessary extracted DNA from the crushed seed material.

Example 2

2. Seeds Softened by Soaking in Alkali and Crushed with Steel Beads

In this experiment the pin crusher device is not employed. Instead the seeds were softened using NaOH or KOH or the like. This whole seed NAOH pretreatment is not to extracting DNA from the whole seed instead it is to soften the seed for fragmentation. DNA extraction with NaOH is a well-known procedure for extracting DNA from disrupted material (leaves, seed chips), but not for softening seeds in a pretreatment step.

a. The seeds were presoaked in solution which softened the seeds so that a pin crusher was not needed. And was therefore not used. 100 mM NaOH, 2000 ul was added at 65° C. to the wells with whole seeds. Being soaked overnight pretreated these seeds. Alternatives to NaOH include such materials as KOH, baking soda (if pH levels are adequately achieved) or any other alkali. Concentrations of these soaking solutions can be varied to be higher or lower depending on the hardiness of the seeds. Also the temperature for pretreatment of the seeds can be varied from 65° C.; higher or lower (even room temperature). The soaking time for pretreatment of the seeds depends on kernel (hardiness), alkali concentration and temperature.

b. Together with the soaking solution, 4 steel beads/well were added to each well with each seed.

c. Unlike Example 1, the pin-crushing step was skipped. No additional liquid was added prior to shaking plates because the addition of liquid may decrease reducer elements impact on seed material in well.

d. After the pretreatment soaking with beads was completed the plate of wells was placed on the horizontal shaking platform.

e. The well plate was shaken for approximately 4 minutes at room temperature. This step can be repeated if necessary. If seed particles are not sufficiently small this step is repeated.

f. The plate with steel ball bearings in each well was removed from the horizontal shaking device. The presoaked seed material within wells was disrupted by the steel bearings in each well.

g. Extract of DNA from the now seed crushed particulates followed the protocol listed in above example. The easiest way was to centrifuge the wells with the extraction solution and, transfer aliquots of supernatant to a new block (e.g. 48 well block), add $NH_4CH_3COO$ and isopropanol, perform DNA precipitation, centrifuge, pour off the supernatant, and perform 70% Ethanol wash.

h. Alternative protocol which could be employed uses 0.25% SDS in NaOH soaking solution. Shake with steel beads. Add $NH_4CH_3COO$ and shake again. Centrifuge and transfer aliquot for alcohol precipitation to new block. (Shaking/Centrifugation with SDS/$NH_4CH_3COO$ gives cleaner DNA). If necessary pH is adjusted (i.e. lowered) for method.

Example 3

3. Presoaked Seeds Pulverized by Solution in the Wells.
1. Presoaked seeds in solution overnight to soften the seeds according to example 1.
2. Placed presoaked seed in a well or seeds can be soaked in well and soaking solution can be poured off. Added several steel beads (no liquid solution), shook in a horizontal shaker (seeds are disrupted) briefly centrifuged to collect debris before opening wells/block.
3. Added liquid (e.g. DNA extraction buffer), shook again in a horizontal shaker, seed were completely crushed.
4. Proceeded with testing as indicated above.

Maize seeds were prepared for DNA extraction by a pretreatment method including soaking in varying concentrations of sodium hydroxide between 0.1M and 0.25 M, varying concentrations of sodium chloride between 1M and 5M, and soaking temperatures between 22° C. and 50° C.

Example 4

Seeds were soaked in a solution containing 3M NaCl and 0.2M NaOH at 35° C. for 21 hours in a well plate. The soaking solution was removed and the seeds were crushed in modified Dellaporta DNA extraction buffer (Dellaporta et al. Plant Mol. Biol. Rep. 1:19, 1983). The figures depicts the well plate containing crushed seeds in extraction buffer after centrifugation. Reducing elements in the form of small steel balls are visible in each well, along with seed residue at the bottom of each well. Supernatant comprising DNA in extraction buffer is visible above the residue in each well.

Example 5

Figure 6:
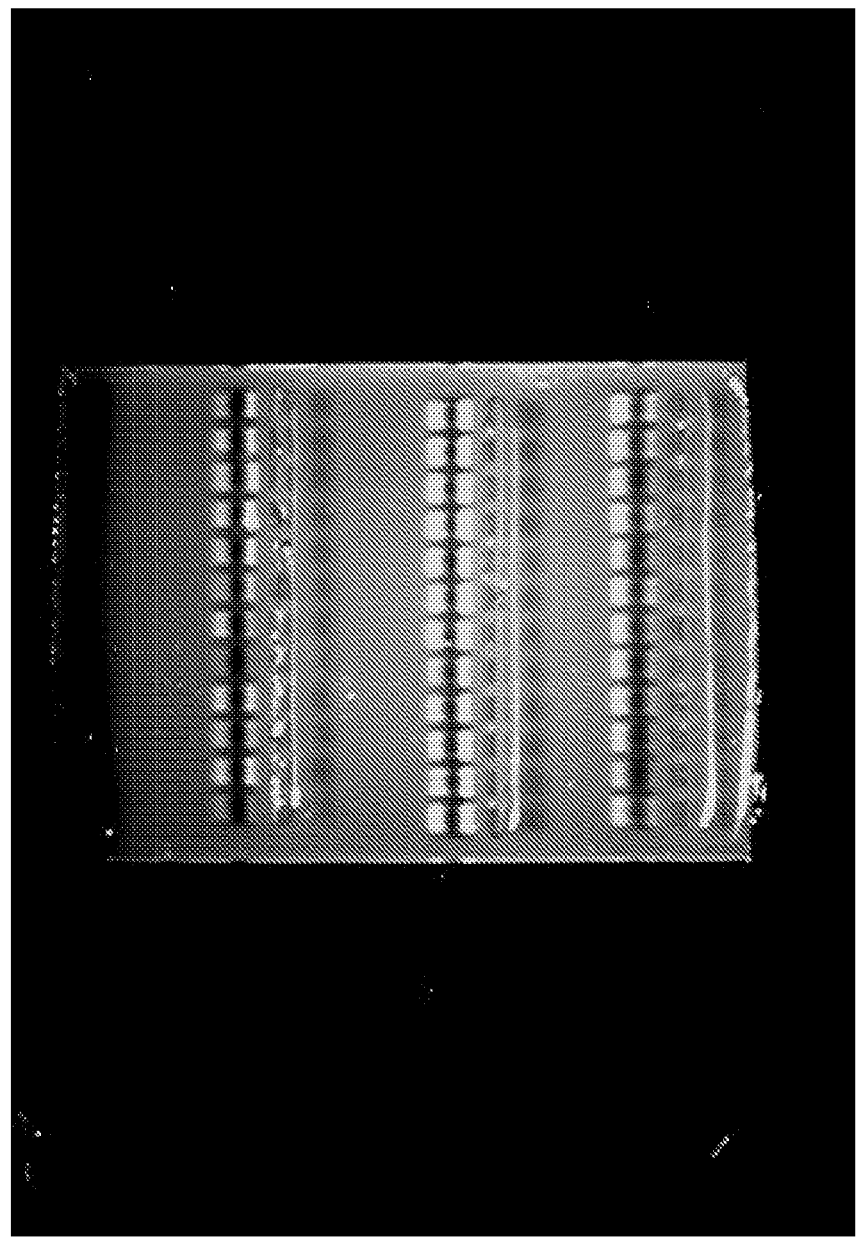
FIG. 6 depicts DNA profiles of the DNA extracted from maize seeds, showing the effect on DNA yield of soaking seeds with different sodium hydroxide concentrations at 22° C. prior to DNA extraction. Lower row: seeds were soaked in extraction buffer (pH 8.2), crushed with a pin crusher and completely fragmentized with steel beads. Middle row: seeds were soaked in 1M sodium chloride and 0.1M sodium hydroxide, then shaken with steel beads in extraction buffer. Upper row: seeds were soaked in 1M sodium chloride and 0.2 M sodium hydroxide, then shaken with steel beads in extraction buffer.

This experiment shows the effect of NaOH concentration on DNA yield at 22° C.: FIG. 6 depicts DNA profiles for the extracted DNA: Lower row: seeds were soaked in a modified Dellaporta extraction buffer (pH 8.2), crushed with a 48 pin crusher and completely fragmentized with steel beads. Middle row: seeds were soaked in 1M NaCl/0.1M NaOH, soaking solution was discarded, modified Dellaporta extraction buffer was added, seeds were shaken with steel beads in a paint shaker, and DNA was extracted using a modified Dellaporta protocol. Upper row: Seeds were soaked in 1M NaCl/0.2M NaOH, soaking solution was discarded, modified Dellaporta extraction buffer was added, seeds were shaken with steel beads in a paint shaker, and DNA was extracted using a modified Dellaporta protocol.

Example 6

Figure 7:
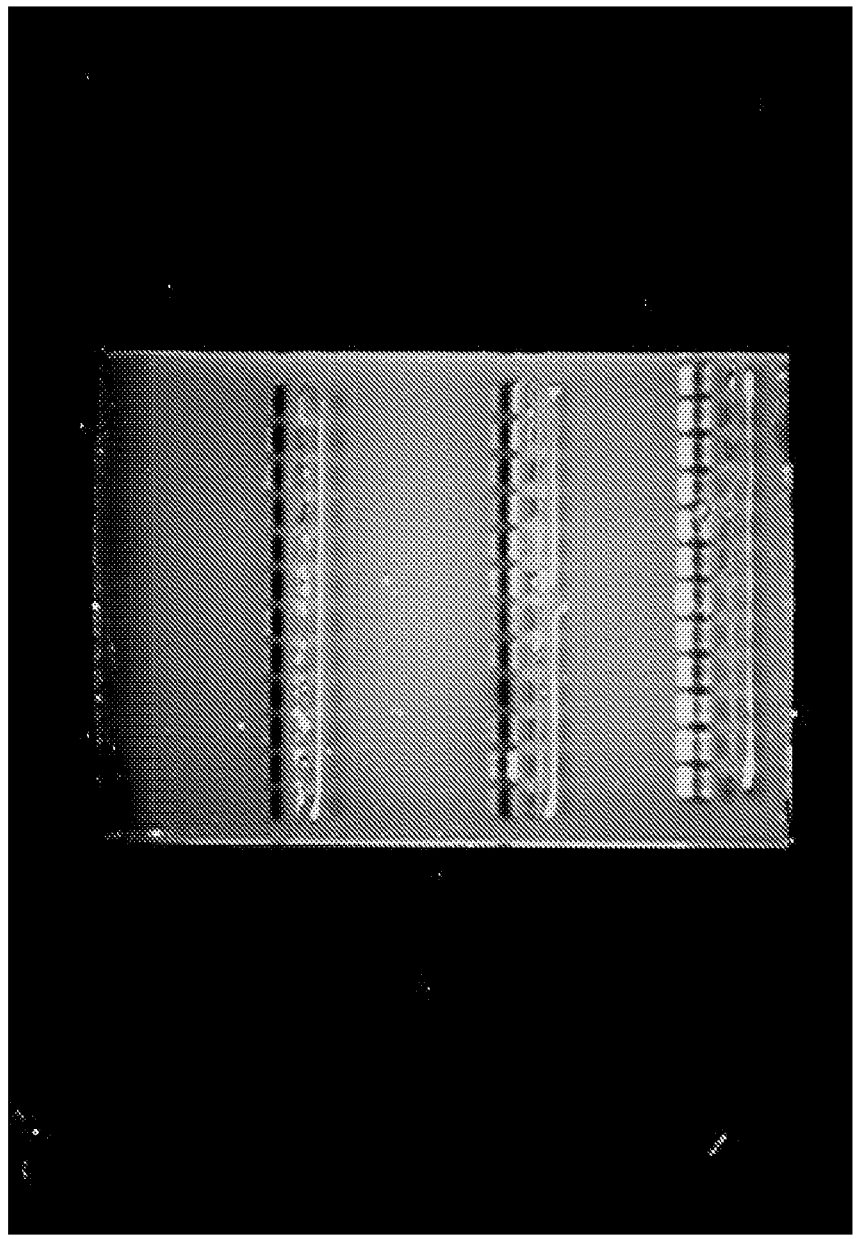
FIG. 7 depicts DNA profiles of DNA extracted from maize seeds, showing the effect on DNA yield of soaking seeds with different sodium hydroxide concentrations at 40° C., prior to DNA extraction. Lower row: seeds were soaked in extraction buffer (pH 8.2), crushed with a pin crusher and completely fragmentized with steel beads. Middle row: seeds were soaked in 1M sodium chloride and 0.1M sodium hydroxide, then shaken with steel beads in extraction buffer. Upper row: seeds were soaked in 1M sodium chloride and 0.2 M sodium hydroxide, then shaken with steel beads in extraction buffer.

This experiment shows the effect of NaOH concentration on DNA yield at 40° C.: DNA from all seed samples were extracted using a modified Dellaporta protocol: FIG. 7 depicts DNA profiles for the extracted DNA: Lower row: Seeds were soaked in a modified Dellaporta extraction buffer (pH 8.2), crushed with a 48 pin crusher and completely fragmentized with steel beads. Middle row: Seeds were soaked in 1M NaCl/0.1M NaOH, soaking solution was discarded, modified Dellaporta extraction buffer was added, seeds were shaken with steel beads in a paint shaker, and DNA was extracted using a modified Dellaporta protocol. Upper row: Seeds were soaked in 1M NaCl/0.2M NaOH, soaking solution was discarded, modified Dellaporta extraction buffer was added, seeds were shaken with steel beads in a paint shaker, and DNA was extracted using a modified Dellaporta protocol.

Example 7

Figure 8:
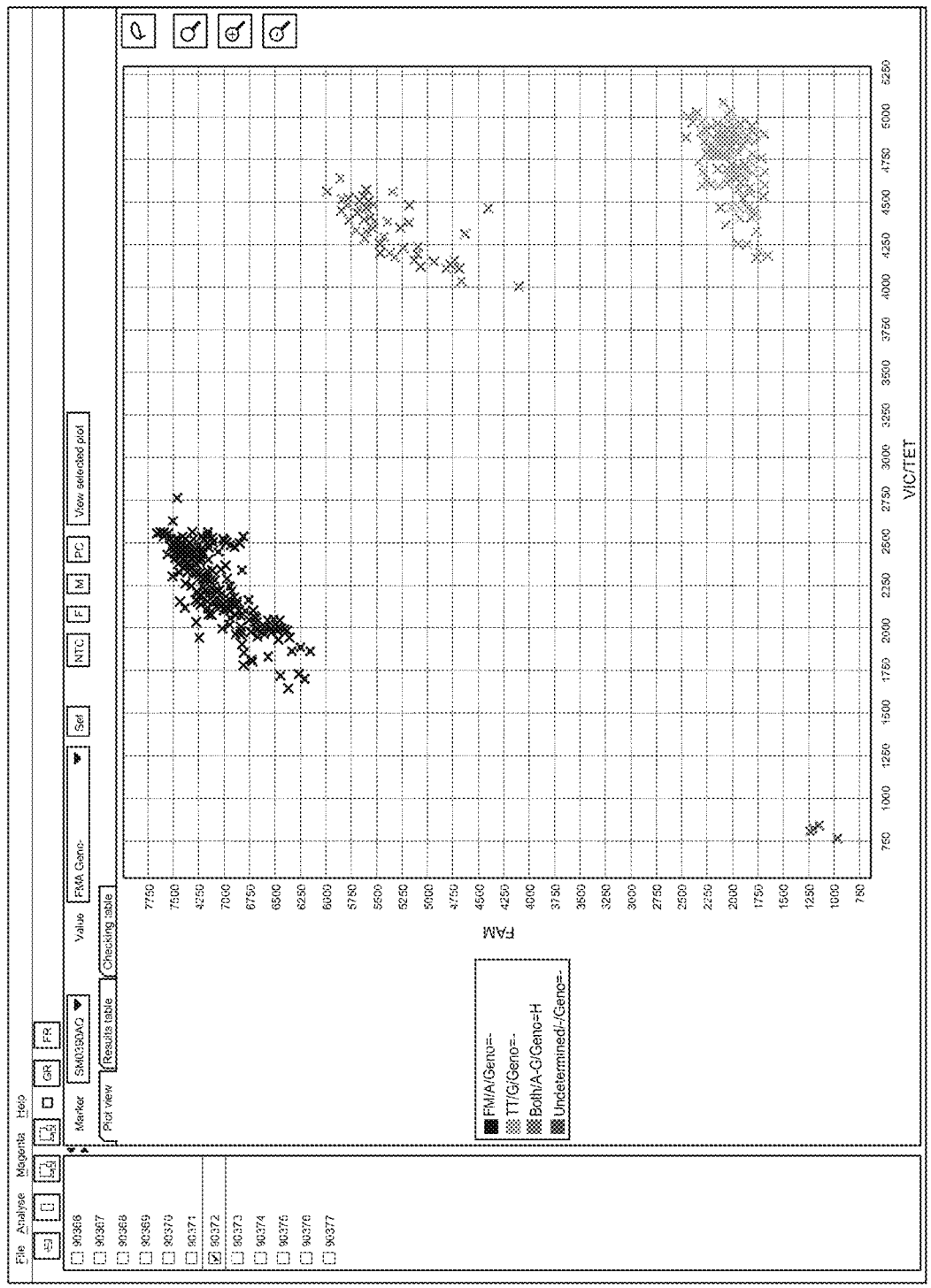
FIG. 8 depicts an allelic discrimination plot for seeds from different seed lots soaked in 3M sodium chloride and 0.2 M sodium hydroxide at 35° C. then shaken with steel beads in extraction buffer. The plot shows the FM/A genotype in the left hand corner, the A and G genotype in the right middle portion and the G genotype in the lower right hand side of the chart, and with a small scattering of undetermined in the lower left side of the chart.

This experiment illustrates results of allelic discrimination using the methods hereof. Seeds from different seed lots were soaked in 3M NaCl/0.2M NaOH at 35° C. The soaking solution was discarded, modified Dellaporta extraction buffer was added, and the seeds were shaken with steel beads in a paint shaker. DNA was extracted using a modified Dellaporta protocol. Extracted DNA was used as a template for Taqman analysis. FIG. 8 shows the results in which three clusters were clearly identified, with a small unidentified genotype shown in the lower left corner of the plot.

The foregoing results showed that increasing the sodium hydroxide concentration of the pretreatment soaking solution and/or the soaking temperature increases the crushing efficiency with steel beads, but lowers the DNA yield. Increasing the sodium chloride concentration of the soaking solution lowers the crushing efficiency but increases the DNA yield.

Example 8

The experiment illustrates differences in DNA yield from use of different minimal soaking amounts. The minimal soaking is for softening of the corn. When employing minimal soaking the seeds are barely or just covered with liquid. These minimal soaking protocols have a fluid range between 200 ul-and 800 ul when the fluid is used to cover or slightly less than cover the seed within the well, the preferred range of fluid is between 400 ul and 600 ul when using a corn seed contained within a 48 well block with a pyramidal bottom. In contrast, when using an osmoticum with a nonminimal soaking fluid amount, in the same size well, the seed was soaking in 1500 ul of the pretreatment fluid.

This experiment shows the effect of soaking volume on DNA yield: Corn seeds were soaked in 400 ul and 600 ul of 0.3 M NaOH/1.5% SDS at 65° C. for 18 hours. After 18 hours, a DNA extraction buffer was added and seeds were crushed with steel beads in a paint shaker. DNA was extracted using a modified Dellaporta extraction method. The results showed excellent DNA yields from 12 seeds soaked in 400 ul. This DNA was plentiful and an allelic discrimination plot was performed with DNA extracted from corn seeds soaked in 0.3M NaOH/1.5% SDS. This allelic discrimination plot showed the usefulness of this DNA with a very clear discrimination. In contrast, the DNA from the seed soaked in 600 ul of 0.3 M NaOH/1.5% SDS at 65° C. for 18 hours had a DNA yield which was substantially less than the yield from the seeds soaked in 400 ul.

This experiment shows effect of soaking volume on DNA yield: Corn seeds were soaked in 400 and 600 ul of 0.3 M NaOH/1.5% SDS at 65° C. for 18 hours. After 18 hours, a DNA extraction buffer was added and seeds were crushed with steel beads in a paint shaker. DNA was extracted using a modified Dellaporta extraction method. The results showed excellent DNA yields from 12 seeds soaked in 400 ul. This DNA was plentiful and an allelic discrimination plot was performed with DNA extracted from corn seeds soaked in 0.3M NaOH/1.5% SDS. This allelic discrimination plot showed the usefulness of this DNA with a very clear discrimination. In contrast, the DNA from the seed soaked in 600 ul of 0.3 M NaOH/1.5% SDS at 65° C. for 18 hours had a DNA yield which was substantially less than the yield from the seeds soaked in 400 ul.

The methods provided herein have been illustrated using specific method steps, reagents and starting materials, however, it will be appreciated by those skilled in the art that equivalent steps, reagents and starting materials can be substituted for those mentioned herein for purposes of illustration, and that the appended claims are intended to cover all such equivalents.

The invention claimed is:

1. A method for extracting and isolating DNA from corn seeds, said method comprising:
   a. pretreating said seeds by soaking the seeds in a pretreatment solution comprising:
      i. an alkali in a concentration sufficient to soften said seed and
      ii. an osmoticum at a concentration in the range of about 1 M to about 5 M, wherein said osmoticum is an aqueous solution of a solute selected from the group consisting of sodium chloride, potassium chloride, a polyethylene glycol (PEG), mannitol, a sugar alcohol, and sucrose;
   b. crushing said seeds;
   c. contacting a DNA extraction buffer with said crushed seeds, whereby said contacting extracts DNA from said crushed seed; and
   d. the DNA solution is isolated and the DNA separated therefrom.

2. The method of claim 1 wherein said alkali is a solution comprising sodium hydroxide or potassium hydroxide.

3. The method of claim 2 wherein said alkali is present at a concentration of about 0.1 M to about 1 M.

4. The method of claim 1 wherein said soaking is continued for a period of time sufficient to soften said seed.

5. The method of claim 1 wherein said soaking is performed at a temperature between about 22° C. and about 65° C.

6. The method of claim 1 wherein said crushing is performed by a method comprising placing said seeds in a confined space and shaking them with size-reducing elements.

7. The method of claim 6 wherein said size-reducing elements are objects have sufficient hardness to break up the seeds.

8. A method for extracting and isolating DNA from corn seeds, said method comprising:
   a. pretreating said seeds by soaking the seeds in a pretreatment solution comprising:
      i. an alkali in a concentration sufficient to soften said seed and optionally
      ii. an osmoticum at a concentration in the range of about 1 M to about 5 M, wherein said osmoticum is an aqueous solution of a solute selected from the group consisting of sodium chloride, potassium chloride, a polyethylene glycol (PEG), mannitol, a sugar alcohol, and sucrose;
   b. crushing said seeds, wherein said crushing is performed by a method comprising placing said seeds in a confined space and shaking them with size-reducing elements;
   c. contacting said crushed seeds with a DNA extraction buffer; and
   d. the DNA solution is isolated and the DNA separated therefrom.

* * * * *

UNITED STATES PATENT AND TRADEMARK OFFICE
CERTIFICATE OF CORRECTION

PATENT NO. : 9,719,893 B2  
APPLICATION NO. : 14/359238  
DATED : August 1, 2017  
INVENTOR(S) : Ulrich Hannappel Page 1 of 1

It is certified that error appears in the above-identified patent and that said Letters Patent is hereby corrected as shown below:

On the Title Page

(72) Inventor last name "Happappel" should be corrected to Hannappel.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*